(12) United States Patent
Kim (10) Patent No.: US 12,279,870 B2
(45) Date of Patent: Apr. 22, 2025

(54) UROFLOWMETRY APPARATUS, MOBILE DEVICE COMPRISING THE SAME AND UROFLOWMETRY METHOD

(71) Applicant: Raai Co., Ltd., Seoul (KR)

(72) Inventor: Young Wook Kim, Seoul (KR)

(73) Assignee: Raai Co., Ltd., Seoul (KR)

( * ) Notice: Subject to any disclaimer, the term of this patent is extended or adjusted under 35 U.S.C. 154(b) by 180 days.

(21) Appl. No.: 18/114,286

(22) Filed: Feb. 27, 2023

(65) Prior Publication Data

US 2023/0270361 A1  Aug. 31, 2023

(30) Foreign Application Priority Data

Feb. 28, 2022 (KR) .......................... 10-2022-0026272
Apr. 12, 2022 (KR) .......................... 10-2022-0045410

(51) Int. Cl.
*A61B 5/20* (2006.01)
*A61B 5/05* (2021.01)

(52) U.S. Cl.
CPC ................. *A61B 5/20* (2013.01); *A61B 5/05* (2013.01); *A61B 2505/07* (2013.01); *A61B 2560/0431* (2013.01); *A61B 2562/04* (2013.01)

(58) Field of Classification Search
CPC ........... A61B 5/20; A61B 5/201; A61B 5/208; A61B 5/05
See application file for complete search history.

(56) References Cited

U.S. PATENT DOCUMENTS

| 2016/0113562 A1* | 4/2016 | Belotserkovsky | A61B 5/202 600/573 |
| 2020/0268302 A1* | 8/2020 | Oh | A61B 5/227 |
| 2024/0108267 A1* | 4/2024 | Koczan | A61B 5/208 |

FOREIGN PATENT DOCUMENTS

| JP | 2004100357 A | * | 4/2004 | |
| JP | 2005290796 A | * | 10/2005 | |
| JP | 2006038873 A | * | 2/2006 | E03D 13/00 |
| JP | 2009036585 A | * | 2/2009 | |
| JP | 2010223772 A | * | 10/2010 | |
| JP | 2015190142 A | * | 11/2015 | |
| JP | 2019148112 A | * | 9/2019 | G01D 5/266 |
| KR | 10-2021-0112646 A | | 9/2021 | |

OTHER PUBLICATIONS

Nasrin, Y. (2021). Detecting Synthetic Urine Leakage Using MmWave Radar. (Year: 2021).*

(Continued)

*Primary Examiner* — Keith M Raymond
*Assistant Examiner* — Johnathan Maynard
(74) *Attorney, Agent, or Firm* — Revolution IP, PLLC (57) ABSTRACT

Disclosed herein is an uroflowmeter which includes: a sensor having a signal transmitter transmitting an input signal to a detection area and a signal receiver receiving an echo signal reflected from urine passing through the detection area; a signal processing unit calculating uroflowmetry data based on a difference between the input signal and the echo signal, the uroflowmetry data being data about a flow of the urine passing through the detection area; and a diagnosis unit diagnosing urinary disorders of a test subject by comparing the uroflowmetry data calculated by the signal processing unit with preset reference uroflowmetry data.

6 Claims, 3 Drawing Sheets

(56) References Cited

OTHER PUBLICATIONS

Qi, Y., Kong, H., & Kim, Y. (2022). Estimation of urine flow velocity using millimeter-wave FMCW radar. Sensors, 22(23), 9402. (Year: 2022).*

Pisa, S., Pittella, E., & Piuzzi, E. (2016). A survey of radar systems for medical applications. IEEE Aerospace and Electronic Systems Magazine, 31(11), 64-81. (Year: 2016).*

* cited by examiner

FIG. 6

UROFLOWMETRY APPARATUS, MOBILE DEVICE COMPRISING THE SAME AND UROFLOWMETRY METHOD

BACKGROUND

The present invention relates to a uroflowmeter, a portable terminal including the same, and a uroflowmetry method and, more particularly, to a uroflowmeter that allows anyone to easily conduct accurate uroflowmetry at home regardless of time and location and can perform accurate diagnosis of various urinary disorders easily and efficiently for each patient by quickly and accurately acquiring urinary flow rate using a non-contact radar sensor instead of a conventional weight measurement method using a weight sensor, a portable terminal including the same, and a uroflowmetry method.

Lower urinary tract symptoms such as dysuria and urinary incontinence include frequent urination, nocturia, delayed urination, interrupted urination, straining to urinate, weak urination, terminal dribbling, post-voiding dribbling, urinary urgency, and urinary incontinence. However, the type and severity of symptoms can vary greatly from person to person.

In order to determine the exact urination pattern of each patient, it is important to determine whether subjective symptoms complained of by patients are real, and objectively assessing severity thereof is crucial for accurate diagnosis. However, urination is an extremely personal physiological activity, making quantification thereof very difficult for clinicians.

When it comes to lower urinary tract symptoms, uroflowmetry is usually the first test performed on almost all patients with lower urinary tract dysfunction. In other words, uroflowmetry can objectively diagnose the presence or absence of lower urinary tract symptoms complained of by patients, such as weak urination, interrupted urination, straining to urinate, and terminal dribbling, as well as the severity of urination disorders.

Conventional uroflowmetry devices and methods are based on measuring the weight of urine. In an exemplary method, changes in weight of urine during urination are measured by accumulating the urine in a constant-diameter container while reading a weight sensor mounted under the container. Measurement of changes in weight of the urine accumulated during urination provides an indication of changes in volume of the urine.

However, in conventional uroflowmetry devices and methods, when a urine stream directly touches the bottom surface of the container in the process of accumulating urine in the container, the bottom surface of the container is additionally impacted by the momentum (mass×velocity) of the urine stream, in addition to the weight of the urine, such that not only the weight of the urine, but also the impulse is transmitted to the weight sensor. The impact effect is randomly transmitted to the weight sensor depending on the amount and velocity of the urine stream, acting as measurement noise. In addition, once a certain amount of urine is collected in the container during urination, an impulse applied to the urine surface is additionally transmitted to the weight sensor, acting as measurement noise.

Furthermore, conventional uroflowmetry devices and methods require uroflowmetry to be performed at a specific place and time, such as in a hospital, for treatment, such that urination cannot be performed in a psychologically stable state without being bothered by others, which can reduce measurement reliability, cause a lot of inconvenience to a test subject as well as a tester during the process of uroflowmetry, and cause a lot of hassle in maintenance of a testing device before and after the test.

In addition, healthcare services that can be provided regardless of time and location are expanding at a rapid pace due to the recent shift from curative to proactive healthcare and the development of information and communication technology (ICT). Therefore, there is a need for a novel uroflowmetry method which allows anyone to easily perform accurate uroflowmetry in their daily life at home, unlike conventional uroflowmetry devices and methods that can only be used in specific places.

SUMMARY

Embodiments of the present invention are conceived to solve such problems in the art and it is an object of the present invention to provide a uroflowmeter that allows anyone to easily conduct accurate uroflowmetry at home regardless of time and location, a portable terminal including the same, and a uroflowmetry method using the same.

It is another object of the present invention to provide a uroflowmeter that is structurally simple and can quickly obtain more accurate uroflowmetry data by a velocity measurement method using a non-contact radar sensor instead of a conventional weight measurement method using a weight sensor, a portable terminal including the same, and a uroflowmetry method using the same.

It will be understood that objects of the present invention are not limited to the above. The above and other objects of the present invention will become apparent to those skilled in the art from the detailed description of the following embodiments in conjunction with the accompanying drawings.

In accordance with one aspect of the present invention, a uroflowmeter includes: a sensor having a signal transmitter transmitting an input signal to a detection area and a signal receiver receiving an echo signal reflected from urine passing through the detection area; a signal processing unit calculating uroflowmetry data based on a difference between the input signal and the echo signal, the uroflowmetry data being data about a flow of the urine passing through the detection area; and a diagnosis unit diagnosing urinary disorders of a test subject by comparing the uroflowmetry data calculated by the signal processing unit with preset reference uroflowmetry data.

The sensor may include at least one selected from among a pulse radar, a continuous wave (CW) radar, and a frequency modulated continuous wave (FMCW) radar.

The uroflowmetry data may include a urinary flow rate at a distal end of a test subject's genitalia, at which the urine is discharged from the test subject.

The uroflowmetry data may include a time-dependent urinary flow rate from beginning to end of urination.

The uroflowmetry data may further include a volume of urine output, wherein the volume of urine output may be calculated based on the urinary flow rate and a radar cross-section (RCS) of the echo signal varying depending on a size of a cross-sectional area of a urine stream.

The uroflowmetry data may further include the number of urine streams.

The sensor may include: a first sensor having a first signal transmitter transmitting a first input signal in a first direction toward the detection area and a first signal receiver receiving a first echo signal reflected from the urine passing through the detection area; and a second sensor having a second signal transmitter transmitting a second input signal in a second direction crossing the first direction toward the detection area and a second signal receiver receiving a second echo signal reflected from the urine passing through the detection area.

The signal processing unit may calculate a velocity of a falling urine stream discharged from the test subject by vector summation of a first urinary flow rate obtained from the first sensor and a second urinary flow rate obtained from the second sensor, wherein the first urinary flow rate is a flow rate of the urine passing through the detection area with respect to the first direction and the second urinary flow rate is a flow rate of the urine passing through the detection area with respect to the second direction.

In accordance with another aspect of the present invention, a portable terminal includes the uroflowmeter set forth above.

In accordance with further aspect of the present invention, a uroflowmetry method includes: transmitting an input signal to a detection area; receiving an echo signal reflected from urine passing through the detection area; calculating uroflowmetry data based on the input signal and the echo signal, wherein the uroflowmetry data is data about a flow of the urine passing through the detection area; and diagnosing urinary disorders of a test subject by comparing the calculated uroflowmetry data with preset reference uroflowmetry data.

The uroflowmetry data may include a urinary flow rate at a distal end of a test subject's genitalia.

The uroflowmetry data may include a time-dependent urinary flow rate from beginning to end of urination.

The uroflowmetry data may further include a volume of urine output, wherein the volume of urine output may be calculated based on the urinary flow rate and a radar cross-section (RCS) of the echo signal varying depending on a size of a cross-sectional area of a urine stream.

The uroflowmeter according to the embodiments of the present invention has a simple structure to be easily installed on/in a toilet bowl at home, such that uroflowmetry data can be acquired in a psychologically stable state without being bothered by others, regardless of time and location, thereby providing improved measurement reliability.

In addition, by using the non-contact radar sensor instead of a conventional weight measurement method using a weight sensor, the uroflowmeter according to the embodiments of the present invention can accurately diagnose various urinary disorders, such as frequent urination, nocturia, delayed urination, interrupted urination, straining to urinate, weak urination, terminal dribbling, post-voiding dribbling, urinary urgency, and urinary incontinence, for each patient.

It will be understood that advantageous effects of the present invention are not limited to the above effects, and the above and other advantageous effects of the present invention will become apparent to those skilled in the art from the detailed description of the following embodiments in conjunction with the accompanying drawings.

DETAILED DESCRIPTION

Hereinafter, preferred embodiments of the present invention will be described with reference to the accompanying drawings. In description of the embodiments, the same components will be denoted by the same terms and the same reference numerals and redundant description thereof will be omitted.

Figure 1:
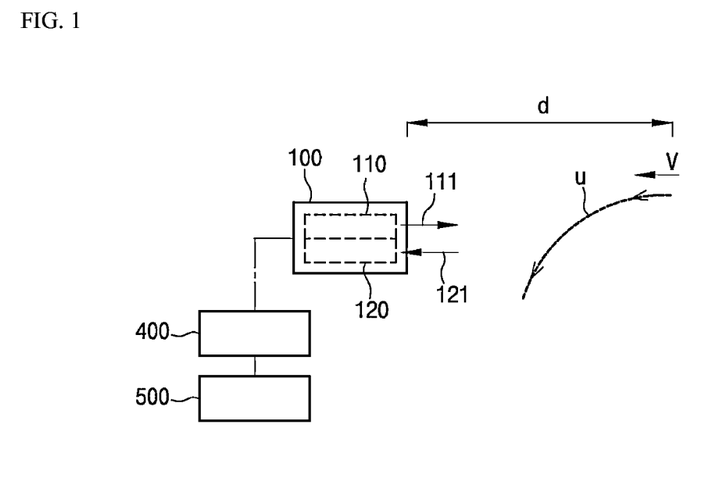
FIG. 1 is a schematic diagram of a uroflowmeter according to one embodiment of the present invention.

FIG. 1 is a schematic diagram of a uroflowmeter according to one embodiment of the present invention.

Referring to FIG. 1, the uroflowmeter according to this embodiment may include a sensor 100, a signal processing unit 400, and a diagnosis unit 500.

The sensor 100 may have a signal transmitter 110 transmitting an input signal 111 to a detection area and a signal receiver 120 receiving an echo signal 121 reflected from urine U passing through the detection area.

The detection area is an area to which the input signal 111 is transmitted, and may correspond to an area through which urine U discharged from a test subject passes. That is, a trajectory of urine may vary from person to person due to differences in body structure and the detection area may be set to an appropriate range in consideration of various possible trajectories of urine.

The sensor 100 may be disposed to face a target (genitalia). That is, the signal transmitter 110 may be disposed to transmit the input signal 111 in a direction facing the direction of discharge of urine U from a test subject.

In addition, the sensor 100 may be disposed at a location spaced apart from the target (genitalia) by a predetermined distance d.

Preferably, the sensor according to this embodiment is a radar sensor.

That is, the signal transmitter 110 may transmit an electromagnetic wave, which is the input signal 111, to the detection area, and the signal receiver 120 may receive an echo wave, which is the echo signal 121 reflected back from a target (urine U).

Then, the signal processing unit 400 may calculate uroflowmetry data, such as the velocity of urine U depending on distance d from the sensor 100, by comparing the transmitted input signal 111 with the received echo signal 121.

That is, the distance d from the sensor to the target (urine) may be calculated from a time difference between transmission of the input signal 111 and reception of the echo signal 121, and the velocity of the target (urine) may be determined from a Doppler shift of the frequency of the echo signal 121. As a result, the radar sensor may measure a distance d-dependent distribution of velocities of the target (urine stream) passing through the detection area and a time-dependent discharge rate V of urine from beginning to end of urination.

Here, the discharge rate V of urine is preferably a urinary flow rate at a distal end of a test subject's genitalia, that is, a urinary flow rate at the moment when urine is discharged from the test subject, in order to remove the influence of gravitational acceleration thereon. A urinary flow rate measured at a distance from the test subject's genitalia is likely to be higher than an actual discharge rate of urine due to the influence of gravitational acceleration, which can lead to diagnostic errors. As such, the urinary flow rate at the distal end of a test subject's genitalia, at which urine is discharged from the test subject, is not influenced by gravitational acceleration and thus may correspond to uroflowmetry data that allows accurate diagnosis of urinary disorders of the test subject.

In this way, the radar sensor may promptly measure and calculate the distance d-dependent distribution of velocities of the target (urine stream) passing through the detection area and the flow rate of urine discharged from a test subject, which is the time-dependent discharge rate of urine from beginning to end of urination, thereby allowing rapid and accurate diagnosis of urinary disorders of the test subject.

When the radar sensor is employed, the signal processing unit 400 may calculate the volume of urine output based on a radar cross-section (RCS) of the echo signal 121.

That is, the radar cross-section (RCS) of the echo signal 121 may vary depending on the size of the target (urine) (the cross-sectional area of a urine stream). Here, the radar cross-section (RCS) may be defined as a power ratio of the echo signal 121 to the input signal 111 for a given distance between the radar sensor and the target. A larger radar cross-section (RCS) indicates a larger power of the echo signal 121.

Accordingly, the signal processing unit 400 may also calculate the total volume of urine output based on the time-dependent discharge rate V of urine from beginning to end of urination, that is, the urinary flow rate, and a value of the radar cross-section (RCS) of the echo signal 121.

The radar cross-section (RCS) of the echo signal 121 received by the signal receiver 120 may vary depending on the frequency of the input signal 111. When the target is urine, as in this embodiment, the input signal 111 may have a frequency in the range of 1 GHz to 100 GHz, preferably a frequency of 77 GHz.

When the radar sensor is employed, the signal processing unit 400 may calculate the number of urine streams (whether a test subject passes a single stream of urine or multiple streams of urine) and may further calculate uroflowmetry data such as the frequency of interruptions during urination and a direct path (trajectory) of a urine stream.

The radar sensor may be classified into a pulse type and a continuous wave (CW) type depending on the method used to modulate the input signal 111. In this embodiment, the sensor may be a pulse radar sensor, or may be a continuous wave (CW) radar sensor. In particular, the sensor may be a frequency-modulated continuous wave (FMCW) radar sensor.

The CW radar sensor is also called "Doppler radar", and not only detects a target but also can measure the velocity of the target. The CW radar sensor does not require pulse modulation and thus has a relatively simple structure, as compared with the pulse radar sensor. In addition, unlike the pulse radar sensor, the CW radar sensor can continuously transmit the input signal without a break in time and thus can continuously operate even while receiving the echo signal 121, and has the advantage of being effective in measuring the velocity of a target. However, since there is no temporal data in the wave of the input signal that the CW radar sensor transmits, the CW radar sensor has difficulty in measuring data about the distance to the target and thus has difficulty in acquiring velocity data across the trajectory of a urine stream.

The FWCW radar sensor overcomes the disadvantages of the CW radar sensor and can acquire data about the distance from the sensor to the target (urine) by applying frequency modulation to the CW radar sensor. That is, the FMCW radar sensor transmits an input signal 111, the frequency of which changes linearly over time, receives an echo signal 121 reflected from the target, and acquires a beat frequency, which is a difference in frequency between the input signal 111 and the echo signal 121. Since the as-acquired beat frequency increases linearly with time delay, the distance from the sensor 100 to the target can be estimated based on the beat frequency. In addition, since the beat frequency is Doppler-shifted depending on a relative velocity of a moving target, it is possible to estimate the relative velocity of the target, that is, the urinary flow rate (discharge rate V of urine), based thereon.

Figure 2:
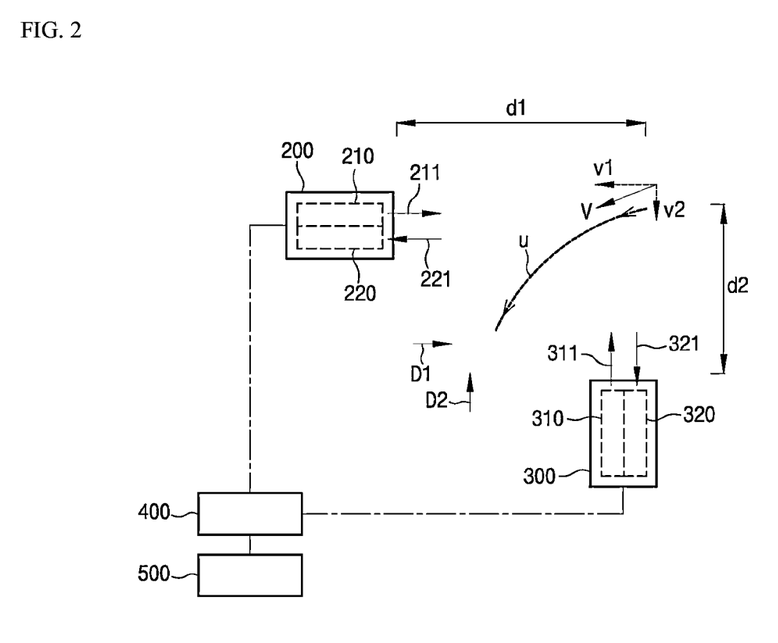
FIG. 2 is a schematic diagram of a uroflowmeter according to another embodiment of the present invention.

FIG. 2 is a schematic diagram of a uroflowmeter according to another embodiment of the present invention.

Referring to FIG. 2, the uroflowmeter according to this embodiment may include multiple sensors, specifically a first sensor 200 and a second sensor 300.

The first sensor 200 may be disposed at a location spaced apart from a target (genitalia) by a first distance d1 and may have a first signal transmitter transmitting a first input signal 211 in a first direction D1 toward a detection area and a first signal receiver 220 receiving a first echo signal 221 reflected from urine passing through the detection area.

The second sensor 300 may be disposed at a location spaced apart from the target (genitalia) by a second distance d2 and may have a second signal transmitter 310 transmitting a second input signal 311 in a second direction D2 crossing the first direction D1 toward the detection area and a second signal receiver 320 receiving a second echo signal 321 reflected from urine passing through the detection area.

That is, a direction in which the first input signal 211 is transmitted from the first sensor 200 may cross a direction in which the second input signal 311 is transmitted from the second sensor 300. Accordingly, the first sensor 200 may estimate a first urinary flow rate v1 with respect to the first direction D1, and the second sensor 300 may estimate a second urinary flow rate v2 with respect to the second direction D2. Then, the signal processing unit 400 may accurately measure a vector value of the urinary flow rate, which is the velocity V of a falling urine stream discharged from a test subject, by vector summation of the first urinary flow rate v1 and the second urinary flow rate v2.

For example, when a male test subject urinates in a standing position into a toilet bowl commonly used at home, if only one sensor is provided to detect a urinary signal in the first direction D1, it may be impossible to properly measure an actual velocity of a urine stream discharged from the test subject depending on the angle of the urine stream.

That is, since the sensor disposed in the first direction D1 only measures a horizontal component of the actual urinary flow rate, depending on the angle of the urine stream discharged from the test subject, even when the actual urinary flow rate of the test subject falls within a urinary flow rate range for normal persons, the measured urinary flow rate may fall within a urinary flow rate range for patients, or vice versa, which results in reduction in accuracy of diagnosis.

In order to prevent such a problem, the uroflowmeter according to this embodiment accurately determines the actual urinary flow rate of the test subject by measuring the velocity V of a falling urine stream discharged from the test subject by vector summation of the first urinary flow rate v1, which is detected by the first sensor 200 disposed in the first direction D1, and the second urinary flow rate v2, which is detected by the second sensor 300 disposed in the second direction D2, thereby further improving the accuracy of diagnosis of urinary disorders.

Although not shown in the drawings, the uroflowmeter according to this embodiment may further include a third sensor, in addition to the first sensor and the second sensor, wherein directions in which respective input signals are transmitted from the third to third sensors may cross each other.

The sensors 100, 200, 300 may be installed on/in a toilet bowl or a bidet. Specifically, the sensors 100, 200, 300 may be embedded in the toilet bowl or the bidet, or may be coupled to a surface of the toilet bowl or the bidet.

For example, when a male urinates in a standing position into a toilet bowl commonly used at home, the sensors may be disposed at a rear end of the toilet bowl or a bidet, which is located in front of a target (genitalia). As another example, when a male or female urinates in a seated position into the toilet bowl, the sensors may be disposed at a front end of the toilet bowl or the bidet, which is located in front of the target (genitalia).

The signal processing unit 400 may be connected to the sensor 100 in a wired or wireless manner and may acquire uroflowmetry data of a test subject by processing and comparing the input signal 111 and the echo signal 121 obtained from the sensor 100.

As described above, the uroflowmetry data may include at least one selected from among the distance-dependent distribution of velocities of a urine stream passing through the detection area, the urinary flow rate (time-dependent discharge rate V of urine), a voiding time, the volume of urine output, the number of urine streams (whether a test subject passes a single stream of urine or multiple streams of urine), the direct path (trajectory) of the urine stream, and the frequency of interruptions during urination.

Figure 3:
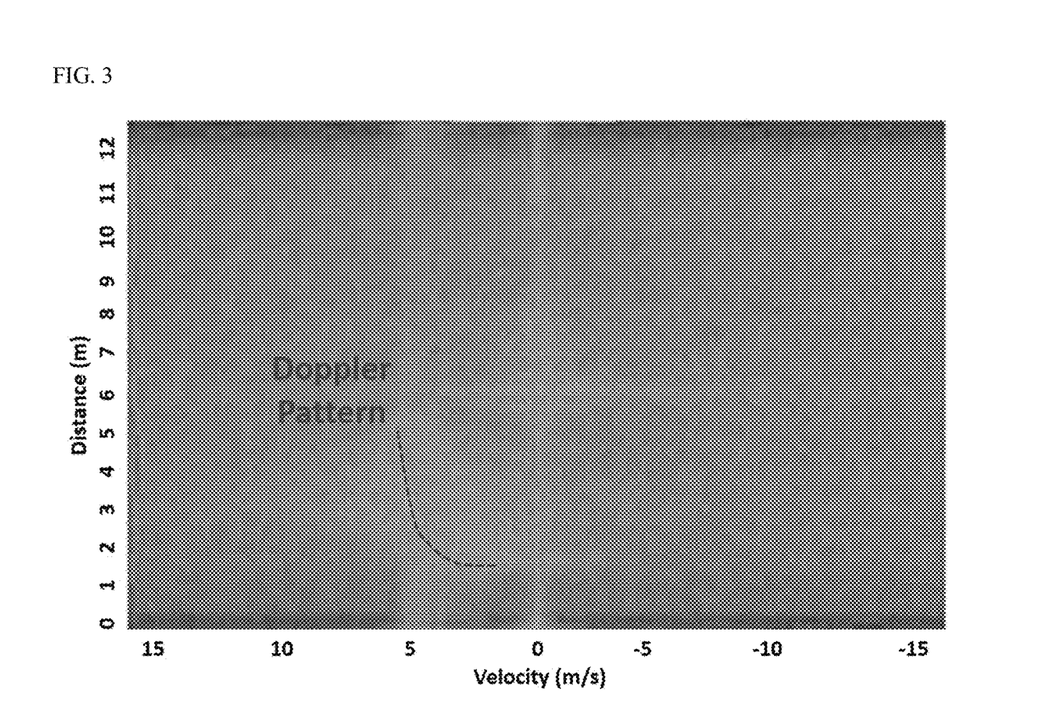
FIG. 3 is a diagram depicting a Doppler-frequency-shifted signal for estimation of the velocity of urine depending on a distance from a sensor.

FIG. 3 is a diagram depicting a Doppler-frequency-shifted signal for estimation of the velocity of urine depending on a distance from the sensor, wherein the vertical axis is a distance from the sensor to a target (urine) and the horizontal axis is a urinary flow rate.

As shown in FIG. 3, since the beat frequency, which is a difference in frequency between the input signal and the echo signal, increases linearly with time delay, it is possible to estimate the distance d from the sensor to a certain point of a urine stream based thereon. In addition, since the beat frequency is Doppler shifted depending on a velocity of the urine stream at the certain point thereof, it is possible to estimate the velocity of the urine stream at the certain point thereof, thereby allowing calculation of a distribution of velocities of the urine stream across the trajectory of the urine stream. In addition, it is possible to calculate the urinary flow rate, which is an initial discharge rate V of urine from a test subject. Further, it is possible to calculate the volume of urine output based on the radar cross-section (RCS) of the echo signal 121. Moreover, it is possible to further calculate various types of uroflowmetry data, such as the number of urine streams (whether a test subject passes a single stream of urine or multiple streams of urine), the frequency of interruptions during urination, and the direct path (trajectory) of the urine stream.

The Doppler frequency-shifted signal, which is indicated in yellow in FIG. 3, is somewhat spread out in the diagram. However, using a high-resolution algorithm, such as a multiple signal classification (MUSIC) algorithm, the accuracy of measurements of a Doppler shift experienced by the beat frequency can be further improved.

In addition, the uroflowmetry data processed by the signal processing unit 400 may be displayed as an image in the diagram. For example, the number of urine streams or the frequency of interruptions during urination can be more intuitively estimated from the imaged uroflowmetry data. In the process of processing the uroflowmetry data into an image, known image classification techniques, such as a convolutional neural network (CNN), may be used to estimate the uroflowmetry data more effectively. The convolutional neural network (CNN) is a deep neural network technique that can effectively process images by applying a filtering technique to an artificial neural network, and is known as a technique for classifying images through a process in which each element of a filter expressed as a matrix is automatically learned to be suitable for data processing.

Figure 4:
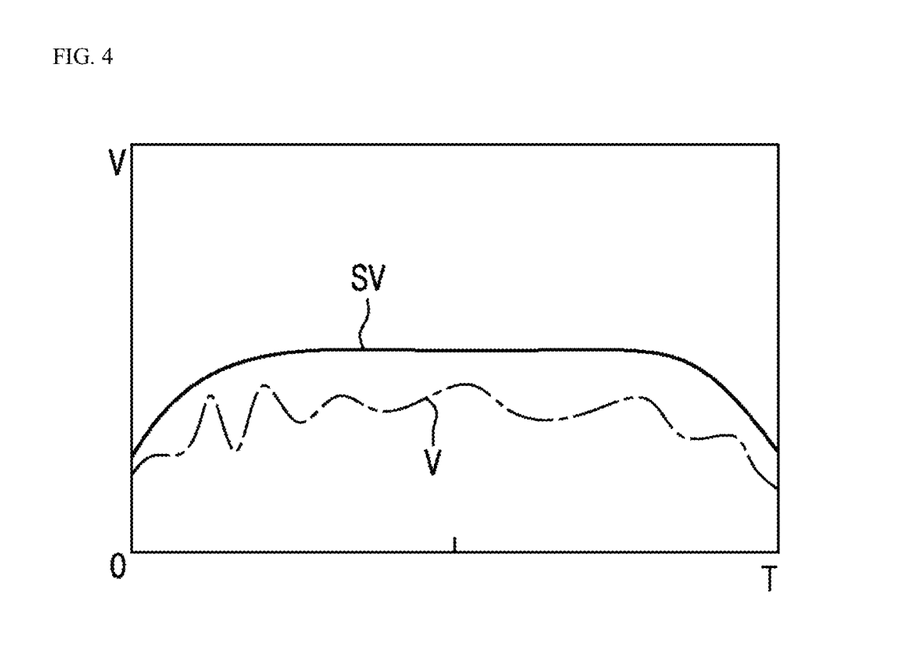
FIG. 4 and FIG. 5 are graphs depicting a time-dependent urinary flow rate calculated by a signal processing unit according to one embodiment of the present invention.
Figure 5:
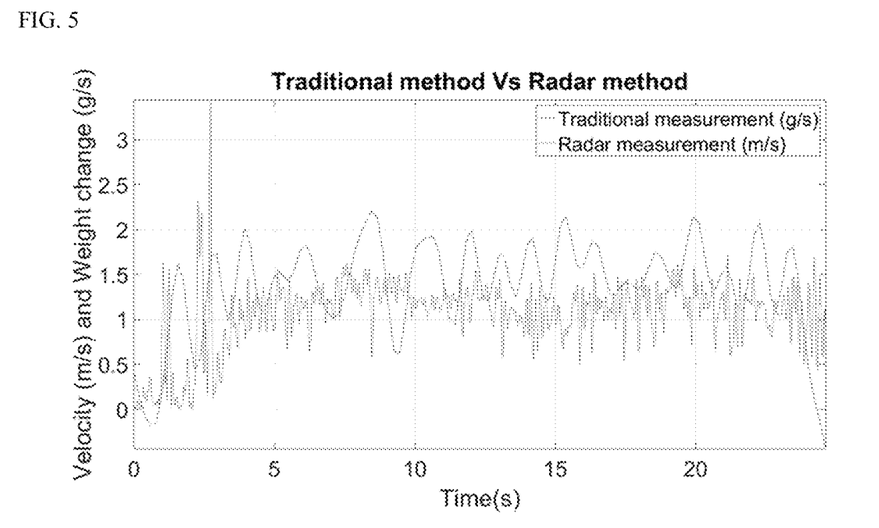

FIG. 4 and FIG. 5 are graphs depicting a time-dependent urinary flow rate calculated by the signal processing unit according to one embodiment of the present invention, wherein the vertical axis is a urinary flow rate and the horizontal axis is time.

Referring to FIG. 4 and FIG. 5, it is possible to diagnose whether or not a test subject has a urinary disorder based on a difference between the time-dependent urinary flow rate V during urination and a reference urinary flow rate SV.

The signal processing unit 400 may further include a signal filter to perform additional filtering of previously processed signals using a function such as a Hanning window function or raised cosine function. For example, there may be a large amount of noise in values of the time-dependent urinary flow rate, which is initially processed by the signal processing unit 400. The signal filter may remove the noise in the values of the time-dependent urinary flow rate to improve the accuracy of measurements of the urinary flow rate.

The diagnosis unit 500 may diagnose a urinary disorder of a test subject by comparing the uroflowmetry data including the urinary flow rate V calculated by the signal processing unit 400 with reference uroflowmetry data including a preset reference urinary flow rate SV.

Here, the reference uroflowmetry data may correspond to uroflowmetry data that can be detected during urination of a normal person. Accordingly, based on a difference between the uroflowmetry data calculated by the signal processing unit 400 and the reference uroflowmetry data, it is possible to determine whether or not a test subject has a urinary disorder.

In other words, the diagnosis unit 500 may compare the uroflowmetry data processed by the signal processing unit 400, such as the distance-dependent distribution of velocities of a urine stream, the time-dependent urinary flow rate, the voiding time, the volume of urine output, the number of urine streams, the direct path of the urine stream, and the frequency of interruptions during urination, with the reference uroflowmetry data obtained from normal persons, such as a reference distance d-dependent distribution of velocities of a urine stream, a reference time-dependent urinary flow rate, a reference voiding time, a reference volume of urine output, a reference number of urine streams (for example, 1), a reference direct path of a urine stream, and a reference frequency of interruptions during urination (for example, 0), and may determine whether or not a test subject has a urination disorder based on comparison results.

In addition, the diagnosis unit 500 may include a storage server, such that the measured and calculated uroflowmetry data can be stored in the storage server to provide continued management of a voiding history of a test subject.

Further, the diagnosis unit 500 may provide diagnostic data to a terminal such as a mobile phone or a tablet computer. Accordingly, a test subject can check the diagnostic data related to the time-dependent urinary flow rate, the voiding time, the volume of urine output, the number of urine streams, the direct path of a urine stream, and the frequency of interruptions during urination, which are displayed on the terminal.

In some embodiments, a portable terminal including the uroflowmeter described above may be provided. Here, the portable terminal may be a mobile phone or tablet computer owned by a test subject.

That is, the test subject can conduct self-diagnose of their urinary disorders without temporal and spatial constraints using the uroflowmeter including the sensor, the signal processing unit, and the diagnosis unit, which is installed in the portable terminal owned by them.

Here, the portable terminal equipped with the uroflowmeter may include an application that allows a test subject to set the location and sensitivity of the sensor, input and modify user data, view self-diagnostic history data, and conduct an online consultation. Accordingly, the test subject can more effectively manage their voiding history using the portable terminal.

Next, a uroflowmetry method according to one embodiment of the present invention will be described.

Figure 6:
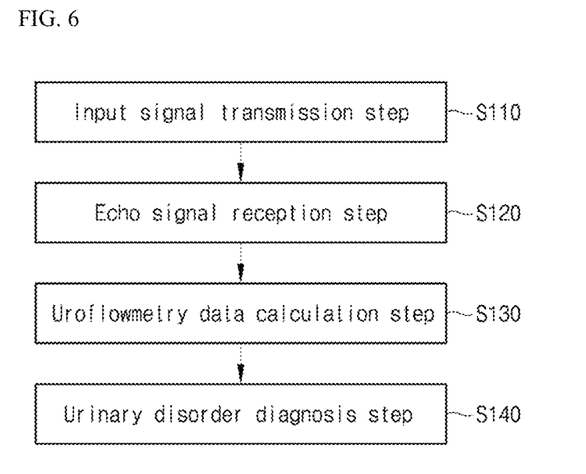
FIG. 6 is a block flow diagram of a uroflowmetry method according to one embodiment of the present invention.

FIG. 6 is a block flow diagram of the uroflowmetry method according to this embodiment.

Referring to FIG. 1 and FIG. 6, the uroflowmetry method according to this embodiment may include an input signal transmission step S110, an echo signal reception step S120, a uroflowmetry data calculation step S130, and a urinary disorder diagnosis step S140.

In the input signal transmission step S110, an input signal 111 is transmitted toward a detection area.

That is, the input signal 111 may be transmitted to the detection area by the signal transmitter 110 of the radar sensor.

In the echo signal reception step S120, an echo signal 121 reflected from urine U passing through the detection area is received.

That is, the echo signal 121 reflected from the urine U may be received by the signal receiver 110 of the radar sensor.

When an FMCW radar sensor is employed, the input signal 111 can be continuously transmitted without a break in time, such that the sensor can operate continuously even while receiving the echo signal 121.

In the uroflowmetry data calculation step S130, uroflowmetry data, that is, data about the flow of the urine U passing through the detection area, is calculated based on the input signal 111 and the echo signal 121.

That is, from a difference in frequency between the transmitted input signal 111 and the received echo signal 121, the signal processing unit 400 may calculate uroflowmetry data including at least one selected from among the distance-dependent distribution of velocities of a urine stream, the time-dependent urinary flow rate, the voiding time, the volume of urine output, the number of urine streams, the direct path of a urine stream, and the frequency of interruptions during urination.

In the urinary disorder diagnosis step S140, a urinary disorder of a test subject is diagnosed by comparing the calculated uroflowmetry data with preset reference uroflowmetry data.

In other words, the diagnosis unit 500 may diagnose whether or not the test subject has a urinary disorder by comparing the uroflowmetry data processed by the signal processing unit 400, such as the distance-dependent distribution of velocities of a urine stream, the time-dependent urinary flow rate, the voiding time, the volume of urine output, the number of urine streams, the direct path of a urine stream, and the frequency of interruptions during urination, with reference uroflowmetry data obtained from normal persons, such as the reference distance-dependent distribution of velocities of a urine stream, the reference time-dependent urinary flow rate, the reference voiding time, the reference volume of urine output, the reference number of urine streams (for example, 1), the reference direct path of a urine stream, and the reference frequency of interruptions during urination (for example, 0).

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

What is claimed is:

1. A uroflowmeter comprising:
a sensor having a signal transmitter transmitting an input signal to a detection area and a signal receiver receiving an echo signal reflected from urine passing through the detection area;
a signal processing unit calculating uroflowmetry data based on a difference between the input signal and the echo signal, the uroflowmetry data being data about a flow of the urine passing through the detection area; and
a diagnosis unit diagnosing urinary disorders of a test subject by comparing the uroflowmetry data calculated by the signal processing unit with preset reference uroflowmetry data,
wherein the uroflowmetry data comprises a urinary flow rate at a distal end of a test subject's genitalia,
wherein the sensor comprises:
a first sensor having a first signal transmitter transmitting a first input signal in a first direction toward the detection area and a first signal receiver receiving a first echo signal reflected from the urine passing through the detection area; and
a second sensor having a second signal transmitter transmitting a second input signal in a second direction crossing the first direction toward the detection area and a second signal receiver receiving a second echo signal reflected from the urine passing through the detection area,
wherein the signal processing unit calculates a velocity of a falling urine stream discharged from the test subject by vector summation of a first urinary flow rate obtained from the first sensor and a second urinary flow rate obtained from the second sensor, the first urinary flow rate being a flow rate of the urine passing through the detection area with respect to the first direction, the second urinary flow rate being a flow rate of the urine passing through the detection area with respect to the second direction.

2. The uroflowmeter according to claim 1, wherein the sensor comprises at least one selected from among a pulse radar, a continuous wave (CW) radar, and a frequency modulated continuous wave (FMCW) radar.

3. The uroflowmeter according to claim 1, wherein the uroflowmetry data comprises a time-dependent urinary flow rate from beginning to end of urination.

4. The uroflowmeter according to claim 1, wherein the uroflowmetry data further comprises a volume of urine output, the volume of urine output being calculated based on the urinary flow rate and a radar cross-section (RCS) of the echo signal varying depending on a size of a cross-sectional area of a urine stream.

5. The uroflowmeter according to claim 1, wherein the uroflowmetry data further comprises the number of urine streams.

6. A portable terminal comprising:
a uroflometer including a sensor having a signal transmitter transmitting an input signal to a detection area and a signal receiver receiving an echo signal reflected from urine passing through the detection area; a signal processing unit calculating uroflowmetry data based on a difference between the input signal and the echo signal, the uroflowmetry data being data about a flow of the urine passing through the detection area; and a diagnosis unit diagnosing urinary disorders of a test subject by comparing the uroflowmetry data calculated by the signal processing unit with preset reference uroflowmetry data,
wherein the uroflowmetry data comprises a urinary flow rate at a distal end of a test subject's genitalia,
wherein the sensor comprises:
a first sensor having a first signal transmitter transmitting a first input signal in a first direction toward the detection area and a first signal receiver receiving a first echo signal reflected from the urine passing through the detection area; and
a second sensor having a second signal transmitter transmitting a second input signal in a second direction crossing the first direction toward the detection area and a second signal receiver receiving a second echo signal reflected from the urine passing through the detection area,
wherein the signal processing unit calculates a velocity of a falling urine stream discharged from the test subject by vector summation of a first urinary flow rate obtained from the first sensor and a second urinary flow rate obtained from the second sensor, the first urinary flow rate being a flow rate of the urine passing through the detection area with respect to the first direction, the second urinary flow rate being a flow rate of the urine passing through the detection area with respect to the second direction.

* * * * *